United States Patent [19]

Lardner

[11] Patent Number: 4,681,132
[45] Date of Patent: Jul. 21, 1987

[54] CHECK VALVE WITH PRESET CRACKING PRESSURE

[75] Inventor: George E. Lardner, North Seminole, Fla.

[73] Assignee: Halkey-Roberts Corporation, St. Petersburg, Fla.

[21] Appl. No.: 867,319

[22] Filed: May 23, 1986

[51] Int. Cl.$^4$ ............................................. F16K 15/14
[52] U.S. Cl. .................................... 137/271; 137/843; 137/903
[58] Field of Search ........................ 137/271, 843, 903

[56] References Cited

U.S. PATENT DOCUMENTS

| 173,318 | 2/1976 | McCarty . | |
|---|---|---|---|
| 1,640,408 | 5/1926 | House . | |
| 1,901,143 | 3/1933 | Brunner . | |
| 2,270,838 | 1/1942 | Langdon . | |
| 3,192,949 | 7/1965 | Desee | 137/540 |
| 3,385,301 | 5/1968 | Harauteneian . | |
| 3,495,594 | 2/1970 | Swanson | 137/843 X |
| 3,513,875 | 3/1968 | Nelson . | |
| 3,807,445 | 4/1974 | McPhee | 137/843 X |
| 3,831,629 | 8/1974 | Mackal . | |
| 3,970,106 | 6/1976 | Harris | 137/843 |
| 4,069,951 | 1/1978 | Winckelmann . | |
| 4,209,485 | 6/1980 | Greenspan . | |
| 4,281,658 | 8/1981 | Child . | |
| 4,296,186 | 10/1981 | Wolf . | |
| 4,429,856 | 2/1984 | Jackson . | |
| 4,445,535 | 5/1984 | Mayfield | 137/903 X |
| 4,449,693 | 5/1984 | Gereg . | |
| 4,602,655 | 7/1986 | Mackal | 137/540 |

Primary Examiner—Robert G. Nilson
Attorney, Agent, or Firm—Dominik, Stein, Saccocio & Reese

[57] ABSTRACT

A check valve is disclosed having a preset cracking pressure. The check valve comprises a valve element reciprocatably positioned within a valve body, both the valve body and the valve element including valve seats which seal together when the valve element is urged forwardly within the valve body. A plug is positioned within the rear of the valve body to constantly urge the valve element forwardly thereby defining a cracking pressure necessary to unseat the valve seats allowing the flow of fluid through the valve body.

7 Claims, 3 Drawing Figures

CHECK VALVE WITH PRESET CRACKING PRESSURE

BACKGROUND OF THE INVENTION

1. Field of the Invention

This invention relates to check valves. More particularly, this invention relates to check valves having a pre-set cracking pressure.

2. Description of the Background Art

Presently, there exist many types of check valves designed to control the one-way flow of a fluid therethrough. More particularly, one predominant type of check valve comprises a ball reciprocatingly positioned within a caged area of a fluid passageway. The flow of fluid in one direction through the passageway is uninhibited (unchecked) as it flows around the ball to exit the passageway. However, in the opposite direction, the flow of fluid forces the ball against a valve seat, thereby inhibiting (checking) the flow of fluid therethrough. Many variations of this basic embodiment of a check valve have been developed over the past many decades that check valves have been in use, each having certain advantages when used in certain applications.

In one application area, check valves, commonly referred to as "catheter" check valves, have been developed to control the one-way flow of a fluid into an inflatable bulb of a catheter or endotracheal tube or in similar relatively low-pressure applications. Indeed, due to the relatively low back pressure exerted on the valve element to urge it against the valve seat, it is usually desirable to provide means for constantly urging the valve element against the valve seat such that the valve remains closed when little or no back pressure is present. Consequently, check valves of this nature have a pre-set cracking pressure which must be exerted on the valve element to unseat itself from the valve seat allowing the flow of the fluid in the unchecked direction.

For example, U.S. Pat. No. 3,831,629, the disclosure of which is hereby incorporated by reference herein, discloses a check valve comprising a valve element which is constantly urged in sealing engagement with a valve seat thereby maintaining the valve in a closed condition even during the complete absence of back pressure exerted on the valve. Moreover, a certain amount of forward cracking pressure must be exerted on the valve element in the unchecked direction to unseat the valve element, allowing the flow of fluid therethrough. As illustrated and discussed in said patent, such positive cracking pressure may be overcome by means of a mechanical instrument, such as a syringe, by fluid pressure, or by a combination of the same.

After more than a decade of experience with the check valve disclosed in said patent, the Assignee of said patent and of this application, has realized that there are some disadvantages associated with the check valve manufactured in accordance with that patent. First, while the valve element may be mass-produced for use in a large variety of valves, differently dimensioned valve bodies or valve elements must be produced in order to provide a variety of valves having different cracking pressures. Consequently, a significant inventory of injection molds and related equipment must be continually developed depending upon the needs of each particular customer. Thus, the ability to provide check valves of this nature with different degrees of cracking pressures necessarily results in an increase in the cost of manufacture because of the inability to produce a universal body usable in conjunction a universal valve element to produce different valves having different cracking pressures.

Therefore, it is an object of this invention to provide an apparatus which overcomes the aforementioned inadequacies of the prior art devices and provides an improvement which is a significant contribution to the advancement of the check valve art.

Another object of this invention is to provide a check valve having a pre-set cracking pressure which maintains the check valve in a closed position even when no back pressure is exerted by the fluid on the valve element to seat the same against the seat of the check valve.

Another object of this invention is to provide a check valve having a pre-set cracking pressure comprising a universal valve element positioned within a universal body such that check valves having different cracking pressures can be produced by utilizing universal injection molds for the body and for the valve element thereby decreasing the cost of manufacture.

Another object of this invention is to provide a check valve having a valve element constantly urged against a valve seat by means of an insertable, apertured plug positioned in the output passageway of the check valve in engagement with the valve element.

Another object of this invention is to provide a check valve comprising a valve element urged against a valve seat by means of an insertable, apertured plug, wherein differently sized plugs may be provided to increase or decrease the cracking pressure of the valve.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention comprises a check valve having a pre-set cracking pressure. More particularly, the check valve of the invention comprises a valve element having a forwardly converging frustro-conical valve seat reciprocatingly positioned within a sleeve-like valve body having a central axial passageway therethrough with a corresponding forwardly converging frustro-conical valve seat in mating engagement with the valve seat of the valve element. The valve seat of the valve element is constantly, resiliently urged into sealing engagement with the valve seat of the axial passageway by means of an insertable, apertured plug.

During use, the check valve of the invention functions to prevent the back flow of fluid through the valve in much the same manner as a conventional check valve. However, the forward flow of fluid, normally uninhibited in conventional check valves, must exert a force sufficient to overcome the cracking pressure of the valve; specifically, sufficient fluid or mechanical pressure must be exerted on the valve element to resiliently compress the valve element against the insertable plug thereby unmating the valve seats and allowing the passage of fluid therebetween.

The axial fluid passageway of the body of the check valve of the invention is designed to receive insertable plugs of different thicknesses without alteration. Consequently, when it is desirable to produce a check valve having minimal cracking pressure, a thin apertured plug is assembled into the universal body to minimally urge the valve element in seating engagement with the valve seat of the fluid passageway. Conversely, when a check valve is needed with maximum cracking pressure, the check valve may be assembled with a thicker apertured plug such that maximum pressure must be exerted on the resiliency of the valve element to urge its valve seat in sealing engagement with the valve seat of the fluid passageway. Obviously, an infinite number of variations between such minimum and maximum may be obtained without departing from the spirit and scope of this invention.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
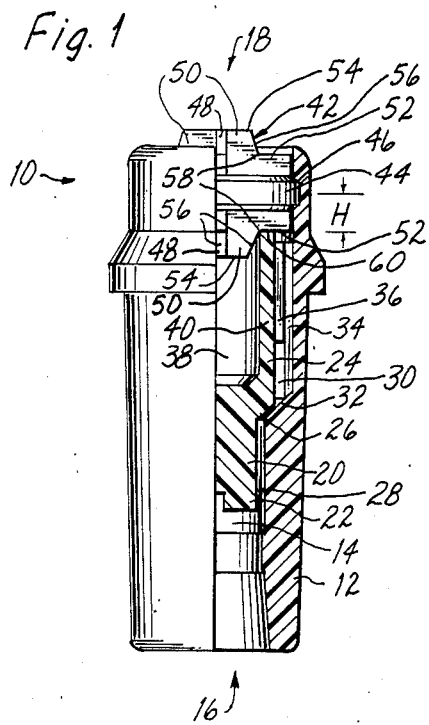
FIG. 1 is a partial cross-sectional view of the check valve of the invention comprising a universal valve element positioned within a universal sleeve-like body by means of a symmetrical, apertured plug.
Figure 2:
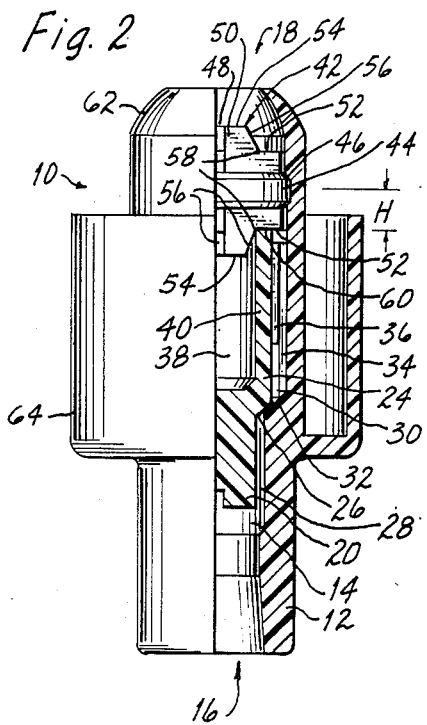
FIG. 2 is another partial cross-sectional view of the check valve of the invention wherein the sleeve-like body further includes a contoured forward end for receiving a tube thereabout and a flanged mounting extending from the outside of the valve body for crimping about the tube after insertion therein.
Figure 3:
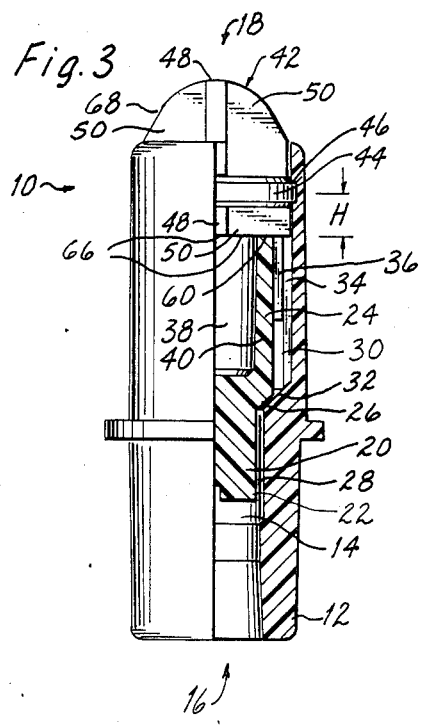
FIG. 3 is still another partial cross-sectional view of the check valve of the invention in which the apertured plug comprises a non-symmetrical, bullet-shaped design to facilitate the insertion of a tube thereover onto the outside surface of the body of the valve.

Referring to FIGS. 1-3, the basic design of the check valve 10 of the invention comprises a sleeve-like integral valve body 12 having a central axial passageway 14 therethrough defining input 16 and output 18. An integral valve element or poppet 20 is reciprocatingly positioned within passageway 14. The valve element 20 comprises a reduced diameter portion 22 and an increased diameter portion 24 joined together at a forwardly converging frustro-conical valve seat 26. Correspondingly, the lumen of the axial passageway 14 comprises a reduced diameter portion 28 and an increased diameter portion 30 joined at a forwardly converging frustro-conical valve seat 32. Valve element 20 is positioned within the axial passageway 14 such that its valve seat 26 is matable against the seat 32 of the body 12 to create an airtight seal therebetween.

The increased diameter portion 30 of the axial passageway 14 comprises a plurality of longitudinal flutes 34 along a portion of the length thereof. Correspondingly, a plurality of longitudinally extending lands or ribs 36 are longitudinally formed on a portion of the outside surface of the increased diameter portion 24 of the valve element 20. However, the number of flutes 34 is different than the number of lands 36 such that the lands 36, combined with the flutes 34, function to centrally locate the valve element 20 within the axial passageway 14. Hence, a more adequate seal is obtained between the respective seats 26 and 32, as more particularly described in U.S. Pat. No. 3,831,629, the disclosure of which has been incorporated by reference herein. Further, the increased diameter portion 24 of the valve element 20 comprises an axial blind hole 38 therein to produce a resilient annular wall 40 capable of flexing when pressure is exerted on the end of the valve element 20.

As described more completely below, the valve element 20 is retained in position within the axial passageway 14 by means of an insertable plug 42 which is properly dimensioned relative to the length of the increased diameter portion 24 of the valve element 20 to compressibly force the seat 26 of the valve element 20 into sealing engagement with the seat 32 of the valve body 12 at a pressure hereinafter referred to as the cracking pressure.

More particularly, referring to FIG. 1, plug 42 comprises a symmetrical design such that the plug 42 can be inserted in the passageway 14 without concern for proper orientation during assembly. The symmetrical plug 42 comprises an annular ring 44 which is engagable within a corresponding annular slot 46 formed within the lumen of the sleeve-like valve body 12. A pair of diametrical vanes 48 and 50, positioned ninety degrees with respect to one another, are integrally formed within the annular ring 44 such that fluid flowing through the passageway 14 flows through the four quadrants or apertures defined by the respective vanes and the annular ring 44. Each of the vanes 48 and 50 comprises a lower annular platform portion 52 and an upper annular platform portion 54 joined at sloping edge 56. The lower corner 58 formed between the sloping edge 56 and the lower platform portion 52 is formed at a diameter substantially equal to the diameter of the blind hole 38 of the valve element 20. With such dimensions, it should be appreciated that the sloping edge 56 of the vanes 48 and 50 of the plug 40 function to centrally locate the rearward end of the valve element 20 within the axial passageway 14 of the check valve 10. Further, the lower annular platform portion 54 provides a flat surface in engagement with the flat rear face 60 of the valve element 20 thereby stablizing the valve element 20 in position within the axial passageway 14.

The check valve 10 of the invention is assembled by simply inserting the valve element 20 into the axial passageway 14 and then snapping into place the plug 42 into the axial passageway 14 until the plug's annular ring 44 engages into annular slot 46. The distance or height of the lower annular platform portion 52 relative to the center of the annular ring 44 of the plug 42, as represented by dimension "H" in FIG. 1, functions to determine the distance between the lower annular platform portion 52 and the valve seat 32 of the valve body 12. Consequently, it should be readily appreciated that increased height H increases the cracking pressure needed to unseat the respective valve seats 26 and 32. Conversely, decreased height H functions to decrease such cracking pressure to a decreased amount. Indeed, height H can be decreased by such a degree that the valve element 20 freely floats within passageway 14 thereby causing the check valve 10 to operate as a conventional check valve with no cracking pressure needed for fluid to flow from the input 16 to the output 18 of the check valve 10.

From the foregoing, it is apparent that the valve body 12 and the valve element 20 may be produced from single sized injection molds utilizing conventional injection molding techniques. However, various plugs 42 may be produced in different injection molds to produce a variety of plugs 42 having different heights H. Thus, during assembly, various check valves 10, each having different cracking pressures, may be assembled by using the appropriate plug 42, thereby maintaining a one-size supply of valve bodies 12 and valve elements 20. Thus, a large variety of check valves having different cracking pressures may be economically supplied to customers without requiring the manufacturer to maintain a large inventory of otherwise different sized valve bodies 12 or valve elements 20.

FIG. 2 illustrates a second embodiment of the check valve 10 in which sleeve-like valve body 12 comprises an extended output end 62 which is crimped inwardly as illustrated to produce a bullet-shaped end. Additionally, the second embodiment of the check valve 10 comprises an annular flanged mounting 64 extending about the central portion of the valve body 12. The second embodiment of this check valve 10 is particularly useful in conjunction with plastic tubing. Specifically, the bullet-shaped end 62 of output 18 allows the check valve 10 to be easily inserted into the end of the tubing (not shown) until the end of the tubing is engaged under the flanged mounting 64. The flanged mounting 64 may then be crimped to securely retain the check valve 10 to the end of the tubing. A more complete disclosure of various types of flanged mountings 64 is disclosed in U.S. patent application, Ser. No. 450,453, filed Dec. 16, 1982, entitled "Self-Retaining Check Valve and Mounting Therefor", which has been assigned to the Assignee of this application, the disclosure of which is hereby incorporated by reference herein.

Finally, FIG. 3 illustrates the third embodiment of the check valve 10 of the invention in which the plug 42 comprises an asymmetrical design having a pair of perpendicularly disposed vanes 48 and 50 integrally formed within an annular ring 44. However, vanes 48 and 50 comprise, on the inward side of the annular ring 44, only one annular platform portion 66 whereas vanes 48 and 50 extending on the outward side of the ring 44 comprise a sloped, bullet-shaped configuration 68. While symmetry and thus, ease during assembly is eliminated, the bullet-shaped edge 68 of the vanes 48 and 50 allows the check valve 10 to be easily inserted into a tubing. Although not illustrated, the third embodiment of the check valve 10 may also include a flanged mounting as shown in FIG. 2 and disclosed in said patent application referenced herein without departing from the spirit and scope of this invention.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit of the invention.

Now that the invention has been described, what is claimed is:

1. A check valve, comprising in combination:
    a valve body having a central axial passageway therethrough defining an input and an output and having valve seat means therein;
    valve element reciprocatingly positioned within said axial passageway, said valve element having valve seat means in sealingly engagable position with said valve seat means of said valve body when said valve element is urged forwardly toward said input and having a resilient rearward portion; and
    a plug positioned within said output of said axial passageway to entrain said valve element within said axial passageway, the distance between said plug and said valve seat means of said axial passageway being appreciably shorter than the distance between the valve seat means of said valve element and said plug, whereby said valve element is urged forwardly to resiliently seal both said valve seat means together thereby defining a cracking pressure necessary to unseat the valve seat means of said valve element and said axial passageway.

2. The check valve as set forth in claim 1, wherein said plug comprises a symmetrical design allowing said plug to be positioned within said output irrespective of which end of said plug is inserted therein.

3. The check valve as set forth in claim 1, wherein said plug comprises an asymmetrical configuration having a bullet-shaped end protruding from said output of said axial passageway to facilitate insertion into a tube or hose.

4. The check valve as set forth in claim 1, wherein said plug comprises an annular ring and a vane positioned diametrically across said vane to define an aperture between said vane and said annular ring.

5. The check valve as set forth in claim 4, wherein said inward edge of said vane comprises a lower annular platform portion and an upper annular platform portion allowing the end of said valve element to be seated upon said lower annular platform portion and centered within said axial fluid passageway by means of said upper annular platform portion.

6. The check valve as set forth in claim 5, wherein said output of said valve body comprises a tapered design.

7. The check valve as set forth in claim 6, wherein said valve body further oomprises a flanged mounting allowing an end of a tube to be inserted therein and rigidly fastened to said valve body.

* * * * *